US005756787A

United States Patent [19]

Schumacher et al.

[11] Patent Number: 5,756,787

[45] Date of Patent: May 26, 1998

[54] PROCESS FOR THE STABILIZATION OF ORGANOTIN HALIDES BY LACTAMS AND/ OR LACTONES AND METAL ALCOHOLATES AND/OR SEMIMETAL ALCOHOLATES AND A GLASS COATING FORMULATION FOR GLASS OR CERAMIC SURFACES

[75] Inventors: Oliver Schumacher, Werne; Ulrich Stewen, Schwerte, both of Germany

[73] Assignee: Witco GmbH, Bergkamen, Germany

[21] Appl. No.: 792,365

[22] Filed: Feb. 3, 1997

[30] Foreign Application Priority Data

Feb. 22, 1996 [DE] Germany ............... 196 06 591.7

[51] Int. Cl.$^6$ ........................................... C07F 7/22
[52] U.S. Cl. ................. 556/2; 556/6; 106/287.19; 427/226; 427/230; 427/255

[58] Field of Search ............. 556/2, 6; 106/287.19; 427/230, 226, 255

[56] References Cited

U.S. PATENT DOCUMENTS

| | | | |
|---|---|---|---|
| 3,424,775 | 1/1969 | Ito et al. | 556/2 X |
| 3,524,846 | 8/1970 | Smith et al. | 556/2 X |
| 4,144,362 | 3/1979 | Larkin. | |

FOREIGN PATENT DOCUMENTS 0 132 024  1/1985  European Pat. Off. .

*Primary Examiner*—Paul F. Shaver
*Attorney, Agent, or Firm*—Scully, Scott, Murphy & Presser

[57] ABSTRACT

Stabilization of alkyltin compounds that are liquid at room temperature, especially alkyltin trihalides, is achieved by addition of 0.1 to 10 wt. % of one or more compounds that are soluble in the alkyltin compounds and that are reactive with water.

15 Claims, No Drawings

PROCESS FOR THE STABILIZATION OF ORGANOTIN HALIDES BY LACTAMS AND/OR LACTONES AND METAL ALCOHOLATES AND/OR SEMIMETAL ALCOHOLATES AND A GLASS COATING FORMULATION FOR GLASS OR CERAMIC SURFACES

BACKGROUND OF THE INVENTION

Liquid alkyltin compounds, especially MBTCl (mono-n-butyltin trichloride) are used as surface-improving agents for glass and other ceramic surfaces.

In order to apply the optically nonperceptible surface-improving layer, the still hot glass surfaces are vapor-treated or sprayed, at 400°–600° C., with a volatile organotin compound after leaving the production machine. At these high temperatures and under the influence of atmospheric oxygen, the organotin substances are pyrolyzed on the glass surface and leave behind a uniform layer of tin oxide.

This protective layer bridges microfissures that arise during the cooling phase, increases the hardness of the glass, and forms the required adhesion layer in order to apply a slip-promoting agent. Bottle-filling output levels of more than 100,000 bottles per hour are possible in breweries, for example, as a result of this surface-improvement technique. It is important, from an economic as well as ecological standpoint, that it has been possible, as a result of this process, to increase the period of usage of multiple-usage bottles and to reduce the weight per bottle.

The use of monoalkyltin halides has already been described in detail in U.S. Pat. No. 4,144,362. It has been found that MBTCl is the optimum surface-improving agent. Relative to inorganic metal halides (e.g., $SnCl_4$, $TiCl_4$), MBTCl has the advantage of a lower susceptibility to hydrolysis and a higher pyrolytic yield.

Industrially, MBTCl is prepared via disproportionation starting with tetra-n-butyltin and $SnCl_4$ with subsequent fractional distillation of the product mixture that is formed and that comprises mono-n-butyltin trichloride and di-n-butyltin dichloride. Although MBTCl can be obtained in high purity via the industrially expensive process of rectification, defects occasionally arise during application in the event of its use as a surface-improving agent for glass.

The cause of this is the formation of solids in the MBTCl storage containers, line systems, and application systems, leading to uncontrollable variations in the quantity applied or even to blockage of the sensitive metering and application system. In such a case, the entire bottle production process has to be stopped, with correspondingly serious economic consequences.

The formation of these solids is due to impurities that remain in traces in the product as a result of the production process and that form insoluble hydrates or hydrolysis products in MBTCl upon exposure to, e.g., atmospheric moisture.

The proposal is made in European Patent No. 132,024 that additives be added to the MBTCl in order to reduce the risk of the deposition of solids. The additives are required to prevent the formation of interfering quantities of these solids, such as crystalline $SnCl_4 \cdot 5\ H_2O$, by dissolving this compound.

According to the proposal there, up to 10 wt. % of additives are added. Compounds from the following classes of substances can be designated as additives: certain alcohols, glycols, glycol ethers, esters, ketones, ethers, aldehydes, anhydrides, formamides, acetates, and nitriles.

The capacity of these additives is rapidly reached and/or exceeded in the event of an accumulation of adverse circumstances, such as higher quantities of production-generated impurities in the product itself and additionally, if applicable, in the containers, lines, and application systems.

Small additional factors that are, in part, not foreseeable or that cannot be influenced, lead again and again to impairment of the production process or the quality of the coatings. The use of larger quantities of these additives is possible but only in a limited manner since the flash point, viscosity, and/or corrosiveness are adversely affected.

A demand for additives therefore exists once again for liquid alkyltin compounds, used as surface-improving agents for glass or ceramic surfaces, whereby the additives should be capable of preventing the formation of undesirable solids more efficiently.

The task of the present invention was therefore to provide compounds that are soluble in liquid alkyltin compounds, especially mono-n-butyltin trichloride (MBTCl), whereby these soluble compounds are capable of preventing the formation of undesirable solids more effectively than the additives used in accordance with the known prior art.

BRIEF SUMMARY OF THE INVENTION

Surprisingly, it has now been found that additives such as carboxylic acid chlorides, certain metal alcoholates or semimetal alcoholates, lactams or lactones, which are soluble in alkyltin compounds and which are capable of hydrolysis, represent stabilizers that can effectively stabilize the alkyltin compounds in distinctly reduced usage concentrations—or, as the case may be, with a corresponding higher capacity—relative to the compounds that are disclosed in the prior art.

One subject of the invention is therefore a process for stabilizing an alkyltin compound that is liquid at room temperature, especially alkyltin trihalide, comprising adding to the alkyltin compound an effective amount, preferably 0.1 to 10 wt. %, and more preferably 0.3 to 3 wt. % of one or more compounds soluble in the alkyltin compound and reactive with water.

A further subject of the invention is glass coating formulations containing one or more alkyltin compounds that are liquid at room temperature, along with 0.1 to 10 wt. %, preferably 0.3 to 3 wt. %, of an additive that is soluble in said one or more alkyltin compounds and that is reactive with water.

Further subjects of the invention are characterized by the claims.

DETAILED DESCRIPTION OF THE INVENTION

The alkyltin compounds useful in accordance with the invention are liquid compounds of general formula (I)

$$(R)_n SnX_{4-n} \qquad (I)$$

in which the following meanings apply: R=alkyl residues with 1–8 C atoms, preferably 1–4 C atoms; X=Cl, Br, I; n=1–4, especially 1, such as dimethyltin dichloride, mono-n-octyltin trichloride and, in particular, mono-n-butyltin trichloride.

Whereas the additives in accordance with the prior art are mere "solvents" whose function is limited to keeping in solution or redissolving the insoluble hydrates or hydrolysis products formed via moisture, the effectiveness of the additives used in accordance with the invention is based in the first instance on preventing even the formation of these hydrates or hydrolysis product. Moisture that is present in, or penetrates into, the system (storage containers, lines) is chemically bound and is thus permanently removed from the system.

The additives of this class that are usable in accordance with the invention are all, accordingly, compounds that react with water and that—under given practical conditions—are soluble in the alkyltin compounds in the form of nonhydrolyzed starting materials and in the form of hydrolyzates after the reaction with water.

The undesirable deposition of solids with quantities of additives that are distinctly reduced relative to the prior art is effectively prevented as a result of the use of these compounds.

Compounds of this class are acid halides of general formula (II)

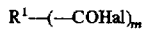
$$R^1\text{—}(\text{—COHal})_m \quad \quad (II)$$

in which $R^1$ is an m-valent, optionally branched, aliphatic, cycloaliphatic or aromatic residue that optionally contains double bonds with 1–10 C atoms; Hal is a halogen atom, especially Cl; and m=1 or 2, such as acetyl chloride, propionyl chloride, cyclohexanoyl chloride, methacryloyl chloride, benzoyl chloride, and adipic acid dichloride.

Other compounds of this class are lactams or lactones of general formula (III)

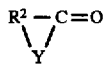
$$\begin{array}{c}R^2\text{—C}=O\\ \diagdown \diagup \\ Y\end{array} \quad \quad (III)$$

in which $R^2$ is a divalent, optionally branched, aliphatic residue with 3–8 C atoms; Y=—O— or —NR$^3$ with $R^3$=preferably H or an alkyl residue with 1–4 C atoms, such as 2-pyrrolidone, N-methyl-2-pyrrolidone, 2-piperidinone, ε-caprolactam, γ-butyrolactone, γ-valerolactone, and ε-caprolactone.

Other compounds of this class are metal alcoholates or semimetal alcoholates of general formula (IV)

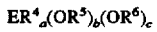
$$ER^4{}_a(OR^5)_b(OR^6)_c \quad \quad (IV)$$

in which E=Si or Ti; a=0–3; b=1–4; c=0–4; and a+b+c=4; $R^4$ can be an optionally branched aliphatic residue that optionally contains multiple unsaturated bonds, with 1–8 C atoms; and $R^5$ and $R^6$ can be identical or different optionally branched alkyl residues with 1–8 C atoms or —C(CH$_3$)=CH—C(O)—CH$_3$ (the acetylacetonate residue), such as tetraethyl titanate, tetra-n-propyl titanate, tetra-i-propyl titanate, tetra-n-butyl titanate, di-isopropoxytitanium bis (acetyl-acetonate), methyltrimethoxysilane, ethyltriethoxysilane, vinyltriethoxysilane, i-propyltriethoxysilane, i-butyltrimethoxy-silane, octyltriethoxysilane, and trimethylethoxysilane.

The compounds of the various classes can be used alone or in the form of mixtures with one another and/or among themselves.

Practice-related quantities of the additives used in accordance with the invention have no negative effects on the quality of the coating on glass. Thus, titanates are used in special applications for improving the surface quality of glass (TiO$_2$ coatings for hardening glass). The SiO$_2$, which is formed via pyrolysis from alkoxysilanes, is in any case a main component of the glass and is present in every SnO$_2$ coating as a result of migration. The carboxylic acid chlorides and the lactams and lactones used along with the corresponding hydrolysis products are pyrolyzed, as is the case with the alkyltin halides themselves, to form CO$_2$, HCl, and H$_2$O. The use of acid chlorides also has the advantage that the formation of MBTCl hydrolyzates is further repressed as a result of the release of equimolar quantities of HCl.

The flash point, corrosiveness, and viscosity of the MBTCl agent for improving the surface quality of glass are not impaired by the additives in accordance with the invention.

EXAMPLES

Example 1

This example shows the capacity of the substances in accordance with the invention for preventing or delaying the occurrence of typical solids in MBTCl.

100 g of MBTCl and 0.5 g of the stabilizer were, in each case, introduced into a 100-mL Erlenmeyer flask with a ground glass stopper in a dry N$_2$ atmosphere and shaken for 5 min.

Afterwards, 0.4 g of SnCl$_4$ and 0.1 mL of deionized water were added to this mixture and again shaken for 5 min. The result was visually evaluated after 18 h.

Evaluation:

"1"=clear, homogeneous liquid that is free of solids

"2"=slight to moderate formation of solids

"3"=intense formation solids

| Stabilizer | Evaluation |
| --- | --- |
| acetyl chloride | 1 |
| propionyl chloride | 1 |
| cyclohexanoyl chloride | 1 |
| methacryloyl chloride | 1 |
| benzoyl chloride | 1 |
| i-propyltriethoxysilane | 1 |
| i-butyltrimethoxysilane | 1 |
| tetraethyl titanate | 1 |
| tetrabutyl titanate | 1 |
| diisopropoxytitanium bis(acetylacetonate) | 1 |
| caprolactam | 1 |
| caprolactone | 1–2 |
| n-propanol-1 (comparative example) | 2 |
| n-butanol-1 (comparative example) | 2 |
| propylene glycol (comparative example) | 2 |
| n-butyl acetate (comparative example) | 3 |
| methyl isobutyl ketone (comparative example) | 3 |
| acetaldehyde (comparative example) | 3 |
| without stabilizer | 3 |

Example 2

This example shows the capacity of the substances in accordance with the invention for wholly or partially redissolving typical solids in MBTCl.

The test method was a modification of the procedure that has been described in European Patent No. 132,024.

100 g of MBTCl, 0.4 g of SnCl$_4$ and 0.1 mL of deionized water was introduced into a 100-mL Erlenmeyer flask with a ground glass stopper and shaken for 5 min. A crystalline precipitate formed.

After 18 h, 0.5 g of the stabilizer was, in each case, added to this mixture and again shaken for 5 min.

After another 18 h, the result was visually evaluated. An evaluation was made as described in Example 1.

| Stabilizer | Evaluation |
| --- | --- |
| acetyl chloride | 1 |
| propionyl chloride | 1 |
| cyclohexanoyl chloride | 1 |
| methacryloyl chloride | 1 |
| n-propanol-1 (comparative example) | 2 |
| n-butanol-1 (comparative example) | 2 |
| propylene glycol (comparative example) | 2 |
| n-butyl acetate (comparative example) | 3 |
| methyl isobutyl ketone (comparative example) | 3 |
| acetaldehyde (comparative example) | 3 |
| without stabilizer | 3 |

We claim:

1. A process for stabilizing an alkyltin compound that is liquid at room temperature, comprising adding to said alkyltin compound an effective amount from 0.1 to 10 wt. % of one or more additives soluble in the alkyltin compound and reactive with water, wherein said one or more additives are selected from the group consisting of acid halides, lactams, lactones, metal alcoholates, semimetal alcoholates and mixtures thereof.

2. A process in accordance with claim 1, wherein said alkyltin compound is an alkyltin trihalide.

3. A process in accordance with claim 1, wherein said one or more additives are selected from the group consisting of one or more acid halides of general formula (II)

$$R^1\text{—}(\text{—COHal})_m \qquad (II)$$

in which $R^1$ is an m-valent, optionally branched, aliphatic, cyclo-aliphatic, or aromatic residue, which optionally contains double bonds, with 1–10 C atoms; Hal is a halogen atom; and m=1 or 2.

4. A process in accordance with claim 1, wherein said one or more additives are selected from the group consisting of lactams and lactones of general formula (III)

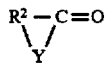

(III)

in which $R^2$ is a divalent, optionally branched, aliphatic residue with 3–8 C atoms; $Y=\text{—O—}$ or $\text{—NR}^3$ and $R^3=H$ or an alkyl residue with 1–4 C atoms.

5. A process in accordance with claim 1, wherein said one or more additives are selected from the group consisting of metal alcoholates and semimetal alcoholates of general formula (IV)

$$ER^4{}_a(OR^5)_b(OR^6)_c \qquad (IV)$$

in which E=Si or Ti; a=0–3; b=1–4; c=0–4; and a+b+c=4; $R^4$ is an optionally branched aliphatic residue that optionally contains multiple unsaturated bonds, with 1–8 C atoms; and $R^5$ and $R^6$ can be identical or different and each is an optionally branched alkyl residue with 1–8 C atoms, or $\text{—C(CH}_3)\text{=CH—C(O)—CH}_3$.

6. A process in accordance with claim 1, comprising adding to said alkyltin compound at least two additives, selected from the group consisting of acid halides of general formula (II)

$$R^1\text{—}(\text{—COHal})_m \qquad (II)$$

in which $R^1$ is an m-valent, optionally branched, aliphatic, cyclo-aliphatic, or aromatic residue, which optionally contains double bonds, with 1–10 C atoms; Hal is a halogen atom; and m=1 or 2; lactams and lactones of general formula (III)

(III)

in which $R^2$ is a divalent, optionally branched, aliphatic residue with 3–8 C atoms; $Y=\text{—O—}$ or $\text{—NR}^3$ and $R^3=H$ or an alkyl residue with 1–4 C atoms; and metal alcoholates and semimetal alcoholates of general formula (IV)

$$ER^4{}_a(OR^5)_b(OR^6)_c \qquad (IV)$$

in which E=Si or Ti; a=0–3; b=1–4; c=0–4; and a+b+c=4; $R^4$ is an optionally branched aliphatic residue that optionally contains multiple unsaturated bonds, with 1–8 C atoms; and $R^5$ and $R^6$ can be identical or different and each is an optionally branched alkyl residue with 1–8 C atoms, or $\text{—C(CH}_3)\text{=CH—C(O)—CH}_3$.

7. A process in accordance with claim 1 wherein mono-n-butyltin trichloride is the alkyltin compound.

8. A process in accordance with claim 7, wherein said one or more additives are selected from the group consisting of one or more acid halides of general formula (II)

$$R^1\text{—}(\text{—COHal})_m \qquad (II)$$

in which $R^1$ is an m-valent, optionally branched, aliphatic, cyclo-aliphatic, or aromatic residue, which optionally contains double bonds, with 1–10 C atoms; Hal is a halogen atom; and m=1 or 2.

9. A process in accordance with claim 7, wherein said one or more additives are selected from the group consisting of lactams and lactones of general formula (III)

(III)

in which $R^2$ is a divalent, optionally branched, aliphatic residue with 3–8 C atoms; $Y=\text{—O—}$ or $\text{—NR}^3$ and $R^3=H$ or an alkyl residue with 1–4 C atoms.

10. A process in accordance with claim 7, wherein said one or more additives are selected from the group consisting of metal alcoholates and semimetal alcoholates of general formula (IV)

$$ER^4{}_a(OR^5)_b(OR^6)_c \qquad (IV)$$

in which E=Si or Ti; a=0–3; b=1–4; c=0–4; and a+b+c=4; $R^4$ is an optionally branched aliphatic residue that optionally contains multiple unsaturated bonds, with 1–8 C atoms; and $R^5$ and $R^6$ can be identical or different and each is an optionally branched alkyl residue with 1–8 C atoms, or $\text{—C(CH}_3)\text{=CH—C(O)—CH}_3$.

11. A process in accordance with claim 7, comprising adding to said alkyltin compound at least two additives selected from the group consisting of acid halides of general formula (II)

$$R^1\text{—}(\text{—COHal})_m \qquad (II)$$

in which $R^1$ is an m-valent, optionally branched, aliphatic, cyclo-aliphatic, or aromatic residue, which optionally contains double bonds, with 1-10 C atoms; Hal is a halogen atom; and m=1 or 2;

lactams and lactones of general formula (III).

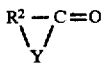 (III)

in which $R^2$ is a divalent, optionally branched, aliphatic residue with 3-8 C atoms; Y=—O— or —$NR^3$ and $R^3$=H or an alkyl residue with 1-4 C atoms; and metal alcoholates and semimetal alcoholates of general formula (IV)

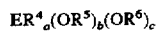 (IV)

in which E=Si or Ti; a=0-3; b=1-4; c=0-4; and a+b+c=4; $R_4$ is an optionally branched aliphatic residue that optionally contains multiple unsaturated bonds, with 1-8 C atoms; and $R^5$ and $R^6$ can be identical or different and each is an optionally branched alkyl residue with 1-8 C atoms, or —$C(CH_3)$=CH—C(O)—$CH_3$.

12. A glass-coating formulation containing one or more alkyltin compounds that are liquid at room temperature, and dissolved therein 0.1-10wt. % of one or more additives that are reactive with water, wherein said one or more additives are selected from the group consisting of acid halides, lactams, lactones, metal alcoholates, semimetal alcoholates and mixtures thereof.

13. A glass coating formulation in accordance with claim 12 wherein the alkyltin compound is mono-n-butyltin trichloride.

14. A glass coating formulation in accordance with claim 12 wherein said one or more additives are selected from the group consisting of acid halides of general formula (II)

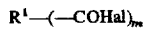 (II)

in which $R^1$ is an m-valent, optionally branched, aliphatic, cyclo-aliphatic, or aromatic residue, which optionally contains double bonds, with 1-10 C atoms; Hal is a halogen atom; and m=1 or 2;

lactams and lactones of general formula (III)

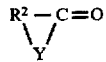 (III)

in which $R^2$ is a divalent, optionally branched, aliphatic residue with 3-8 C atoms; Y=—O— or —$NR^3$ and $R^3$=H or an alkyl residue with 1-4 C atoms; and metal alcoholates and semimetal alcoholates of general formula (IV)

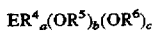 (IV)

in which E=Si or Ti; a=0-3; b=1-4; c=0-4; and a+b+c=4; $R_4$ is an optionally branched aliphatic residue that optionally contains multiple unsaturated bonds, with 1-8 C atoms; and $R^5$ and $R^6$ can be identical or different and each is an optionally branched alkyl residue with 1-8 C atoms, or —$C(CH_3)$=CH—C(O)—$CH_3$.

15. A process for the preparation of a tin oxide layer on a glass or ceramic surface comprising applying to said surface, while said surface is at 400°-600° C., a formulation comprising an organotin trihalide and 0.1 to 10 parts by weight per 100 parts by weight of total formulation of at least one additive that is soluble in the organotin trihalide and that is reactive with water, wherein said one or more additives are selected from the group consisting of acid halides, lactams, lactones, metal alcoholates, semimetal alcoholates and mixtures thereof.

* * * * *